United States Patent
White et al.

(10) Patent No.: US 6,281,382 B1
(45) Date of Patent: Aug. 28, 2001

(54) PALLADIUM PHENANTHROLINE ACETATE CATALYST AND A METHOD OF OXIDIZING SIDE-CHAINS OF ALKYLBENZENES WITH CATALYST

(75) Inventors: Mark G. White, Woodstock; Alexei V. Iretski, Atlanta, both of GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

(21) Appl. No.: 09/585,458

(22) Filed: Jun. 1, 2000

(51) Int. Cl.$^7$ ............ C07C 51/265; C07C 69/773; C07C 45/36; C07C 27/10
(52) U.S. Cl. ............ 562/412; 560/106; 560/113; 568/320; 568/431; 568/815
(58) Field of Search ............ 562/412; 560/106, 560/113; 568/320, 431, 815; 502/162

(56) References Cited

U.S. PATENT DOCUMENTS 4,786,714 * 11/1988 Drent .
4,788,279 * 11/1988 Drent .
5,981,420 * 11/1999 Nakano et al. .

* cited by examiner

Primary Examiner—Paul J. Killos
Assistant Examiner—Robert W. Deemie
(74) Attorney, Agent, or Firm—Todd Deveau; Ryan A. Schneider; Troutman Sanders LLP

(57) ABSTRACT

The method of oxidizing the alkyl groups of alkylbenzenes using palladium phenanthroline acetate or a palladium acetate with modified phenanthroline ligand catalyst. The palladium acetate catalyst with modified phenanthroline has the following formula:

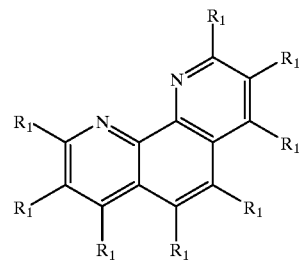

wherein $R_1$ is selected from the group consisting of alkyl groups of from 1 to 3 carbon atoms, OH, and $NO_2$ groups and halogen and hydrogen atoms with at least six of the $R_1$ groups being hydrogen atoms in the ligand.

7 Claims, No Drawings

PALLADIUM PHENANTHROLINE ACETATE CATALYST AND A METHOD OF OXIDIZING SIDE-CHAINS OF ALKYLBENZENES WITH CATALYST

BACKGROUND OF THE INVENTION

1. Field of the Invention

The present invention relates to a new catalyst and is used in the oxidizing of side-chains of alkylbenzenes.

2. Background of the Invention

The oxidation of some alkyl arenes is known to proceed by a radical mechanism. For example, the oxidation of Ar—$CH_3$ by Co(III), ~0.1 M, proceeds at 90–100° C. in oxygen (0.2–1 bar) by the following mechanism.

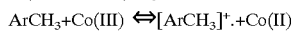

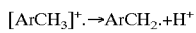

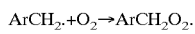

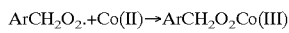

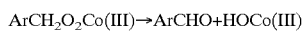

Thus, this reaction mechanism predicts the formation of the aldehyde from the arene without the alcohol as the intermediate product. The aldehyde is converted to the acid by the auto-oxidation.

SUMMARY OF THE INVENTION

Briefly described, in a preferred form, the object of this invention is to oxide the side-chain of alkylbenzenes rather than oxidizing the phenyl carbons. The object of this invention has been achieved by the use of palladium phenanthroline acetate, or a palladium acetate catalyst with a modified phenanthroline ligand as a catalyst. It is used in the presence of oxygen to oxidize the side-chain of alkylbenzenes.

These and other objects, features, and advantages of the present invention will become more apparent upon reading the following specification in conjunction with the accompanying drawing figures.

DETAILED DESCRIPTION OF THE PREFERRED EMBODIMENT

Preparation of the Catalyst

The palladium phenanthroline acetate catalyst is prepared from a divalent palladium (Pd(II)) complexed by 1, 10-phenanthroline. This catalyst may be prepared ex site by traditional wet chemistry methods from the acetate salt or, it may be prepared ill sitsi by combining equimolar amounts of palladium acetate [Pd(Oac)$_2$] and 1, 10-phenanthroline in the reaction mixture just prior to heating the reactants. The critical agent for the novel catalysis is the phen ligand. The effect of the ligand on conversion and selectivity is shown in Table 1:

TABLE I

| Ligand system | (OAc)/Hacac | Oac/phen |
|---|---|---|
| Duration, hours | 4 | 4 |
| Temperature, C. | 150 | 150 |
| Pd/substrate | 0.001 | 0.0015 |
| Oxidant pressure, psig | 750 | 750 |
| Conversion[A] | 7400% | 2290% |

TABLE I-continued

| Ligand system | (OAc)/Hacac | Oac/phen |
|---|---|---|
| Products | | |
| Acetic acid, phenyl ester | 0[B] | 7[C] |
| Benzaldehyde | 0 | 9 |
| Benzyl alcohol | 0 | 6 |
| Benzyl benzoate | 0 | 38 |
| Benzoic acid, phenyl ester | 0 | 4 |
| 2,2'-dmbp | 2 | 2 |
| 2,3'-dmbp | 13 | <1 |
| 2,4'-dmbp | 10 | <1 |
| 3,3'-dmbp | 27 | <1 |
| 3,4'-dmbp | 35 | <1 |
| 4,4'-dmbp | 13 | <1 |
| Methyl benzoate | 0 | 11 |
| 2-methyl phenol | 0 | 4 |
| phenol | 0 | 3 |
| Others | 0 | 11 |

[A]conversion based on equivalents of Pd, %;
[B]yields based on calibrated GC:
[C]yields based on area %

A palladium acetate catalyst with modified phenanthroline ligand of the following formula can also be utilized:

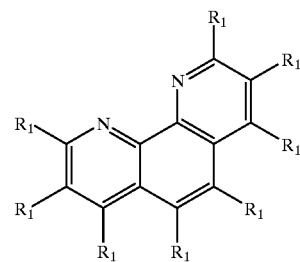

wherein $R_1$ is selected from the group consisting of alkyl groups of from 1 to 3 carbon atoms, OH, and $NO_2$ groups and halogen and hydrogen atoms with at least six of the $R_1$ groups being hydrogen atoms in the ligand.

It is preferred that all of the $R_1$ groups be hydrogen or hydrogen and one or two methyl groups.

Use of the Catalyst

The palladium phenanthroline acetate catalyst is used in the oxidation of aromatic compounds. This catalyst shows a preference for oxidizing benzyl carbons rather than oxidizing phenyl carbons in substituted, aromatic compounds. One example of this new catalysis is the catalytic oxidation of toluene to benzyl benzoate by the following stoichiometry:

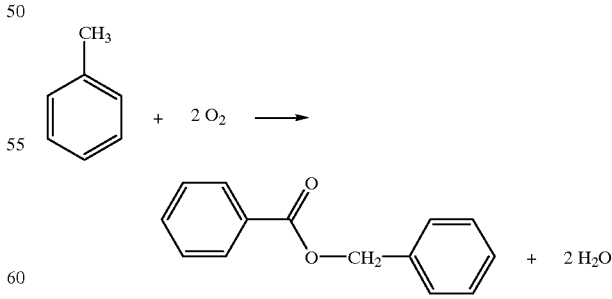

Reaction Conditions

The reaction conditions are mild. Temperature is 100–200° C., pressurized oxygen is the oxidant (500–750 psig) in a mixture with $N_2$ (preferably about 50 mol %). Catalyst to substrate ratio is 0.001–0.003 mol/mol and the reaction may be completed without a solvent. Reaction times in a batch reactor are less than 4 hours. Solvents may be used provided that reactive carbons are not present in these solvents. The effect of the phen ligand is to alter the point of the oxidation to the benzyl carbon and away from the phenyl carbon. Without the phen ligand, the oxidation point is the phenyl carbon when the ligand is (Oac), (acac), and others.

The following compounds were oxidized: toluene, o-xylene, m-xylene, p-xylene, and mesitylene. All reactions were completed in autoclaves of 25–75 cm$^3$ volume using pressurized, artificial air (50-mol % $O_2$) at 750 psig as the oxidant. In a typical reaction 1 mmol of $Pd^2 (OAc)_2$ was introduced with an equimolar amount of 1, 10-phenanthroline into 300 mmol of substrate at room temperature and then the temperature was increased quickly to 150 C.

The Oxidation of the Methylbenzene

The results of the oxidation of toluene, o-, m-, p-xylene, and mesitylene are shown in Table II. These data are shown as turnovers of reactant to give a particular product. The units of the table entries are moles of toluene converted to the indicated species/mole of $Pd^{2+}$ ion. In the case of toluene the methyl group is oxidized to the alcohol, aldehyde, acid, and the ester in significant yields; whereas, the coupled products are always present in smaller amounts. When the substrate was o-xylene, the products where the corresponding alcohol (2-methylbenxyl alcohol), acid (2-methylbenzoic acid) and ester (2-methylbenzoic acid, 2-methyl benzoic ester). The aldehyde product (2-methylbenzylaldehyde) was not observed. Small amounts of the coupled product were observed (3, 4, 3', 4'-tetramethylbiphenyl) and the dealkylated, coupled product (2, 2'-dimethylbibenzyl). Phthalide was observed in modest yields (~1 turnover) at each reaction time. Only two products were observed in significant yields for the oxidation of m-xylene: 3-methylbenzaldehyde and 3-methylbenzoic acid. The oxidation products in significant yields from p-xylene include 4-methyl benzyl alcohol, 4-methylbenzaldehyde, 4-methylbenzoic acid and the ester. Products appearing in small yields are the coupled products and terephthalic aldehyde. In the case of mesitylene as the substrate, the primary products are 3, 5-dimethylbenzyl alcohol, and 3, 5-dimethylbenzaldehyde; whereas the minor product is 2, 4, 6-trimethylphenol.

TABLE II

Turnovers for the Oxidation of Different Substrates with Primary Alkyl Carbons

| Reactant | Product: CH₂OH-C₆H₄-R' | CHO-C₆H₄-R' | COOH-C₆H₄-R' | R-C₆H₄-C₆H₄-R' | R'-C₆H₄-CH₂-OOC-C₆H₄-R' | benzodioxole-type | Sum |
|---|---|---|---|---|---|---|---|
| R = CH₃, R' = H | | | | | | | |
| 15 min | 2.4 | 4.6 | 2.8 | 0.7 | 0.8 | — | 11.3 |
| 45 min | 2.8 | 6 | 4.2 | 0.4 | 1.4 | — | 14.8 |
| 120 min | 2.2 | 6.8 | 6.5 | 0.3 | 3 | — | 18.8 |
| 240 min | 1 | 5.5 | 7 | 0.4 | 9 | — | 22.9 |
| R = CH₃, R' = 2-CH₃ | 2-Me—C₆H₅CH₂OH | 2-Me—C₆H₅CHO | 2-Me—C₆H₅COOH | | 2-Me—C₆H₅COO—CH₂—C₆H₅-2-Me | | |
| 15 min | 5.4 | — | 2.2 | coupled prod. | 0.4 | 1.1 | 9.5 |
| 60 min | 6 | — | 10.4 | 0.4 | 2 | n/a | 18.9 |
| 180 min | 2.8 | — | 4.7 | 0.5 | 1.2 | 1.0 | 9.9 |
| 240 min | 1.6 | — | 2.9 | 0.2 | 0.7 | 1.1 | 6.4 |
| R = CH₃, R' = 3-CH₃ | 3-Me—C₆H₅CH₂OH | 3-Me—C₆H₅CHO | 3-Me—C₆H₅COOH | | 3-Me—C₆H₅COO—CH₂—C₆H₄-3-Me | | |
| 15 min | — | 8.1 | 1.9 | coupled prod. | — | — | 10.0 |
| 45 min | — | 7.6 | 1.9 | 0.1 | — | — | 9.2 |
| 180 min | — | 10.3 | 5.4 | — | — | — | 15.7 |
| 240 min | — | 8.8 | 10.0 | — | — | — | 18.8 |

TABLE II-continued

Turnovers for the Oxidation of Different Substrates with Primary Alkyl Carbons

| Reactant | Product | | | | | | Sum |
|---|---|---|---|---|---|---|---|
| | CH₂OH-C₆H₄-R' | CHO-C₆H₄-R' | COOH-C₆H₄-R' | R-C₆H₄-C₆H₄-R' (coupled prod.) | OHC-C₆H₄-CHO | R'-C₆H₄-CH₂-OOC-C₆H₄-R' | |
| R = CH₃, R' = 4-CH₃ | 4-Me—C₆H₄CH₂OH | 4-Me—C₆H₄CHO | 4-Me—C₆H₄COOH | | | 4-Me—C₆H₅COO—CH₂—C₆H₄-4-Me | |
| 15 min | 14.1 | 14.8 | 13.8 | 0.27 | | 1.1 | 44.2 |
| 45 min | 14.4 | 14.5 | 14.0 | 0.28 | | 1.1 | 44.4 |
| 120 min | 6.0 | 12.6 | 13.2 | 0.2 | | 2.5 | 34.6 |
| 240 min | 4.1 | 14.2 | 24.0 | 0.3 | | 5.4 | 48.1 |
| 3,5-dimethylbenzene | 3,5-Me₂-C₆H₃-CH₂OH | 3,5-Me₂-C₆H₃-CHO | | | | 2,4,6-trimethylphenol | |
| 15 minutes | 10.9 | 19.5 | | | 0.1 | 0.5 | 30.9 |
| 45 minutes | 11.6 | 20.7 | | | 0.1 | 0.5 | 32.8 |
| 120 minutes | 9.9 | 20.0 | | | 0.1 | 0.4 | 30.3 |
| 240 minutes | 10.3 | 22.9 | | | 0.1 | 0.5 | 33.7 |

Oxidation of Ethylbenzenes

The results of the oxidation of ethylbenzene and 4-ethyltoluene are shown in Table III. Acetophenone is the only product for the oxidation of ethylbenzene. When the radical cavenger BHT is added to the reactant mixture in amounts of 1 and 10 wt %, the turnovers to acetophenone decrease by the a factor of 2–3. The oxidation of 4-ethyltoluene shows p-methylacetophenone and p-tolylethanol as the major products with 4-methyl benzaldehyde and 4-ethylbenzyl alcohol as minor products.

Oxidation of o-xylene produced 2-methylbenzyl alcohol and 2-methylbenzoic acid as intermediates to the ester: 2-methylbenzoic acid-2-methyl benzoic acid ester. No aldehyde was observed, but a product of the aldehyde was observed: phthalide.

Oxidation of m-xylene led to only two products: 3-methylbenzaldehyde and 3-methyl benzoic acid. No alcohol was observed, nor was any ester product.

Oxidation of p-xylene leads major products of p-methylbenzyl alcohol, p-methylbenzaldehyde, and p-methyl benzoic acid. The final product is 4-methyl benzoic

TABLE III

Turnovers for the Oxidation of Different Substrates with Secondary Alkyl Carbons

| Reactant | Product | | | | |
|---|---|---|---|---|---|
| CH₂—CH₃ / R' | C(=O)CH₃ / R' | CH₂CH₂OH / R' | CHO / R' | CH₂CH₃ / CH₂OH | Total |
| R' = H, | | | | | |
| 240 minutes | 9.9 | | | | |
| R' = CH₃ | | | | | |
| 15 minutes | 7.0 | 12.5 | 2.0 | 2.9 | 24.4 |
| 45 minutes | 6.3 | 13.7 | 2.1 | 2.8 | 24.9 |
| 120 minutes | 8.2 | 19.9 | 1.9 | 3.9 | 33.9 |
| 240 minutes | 10.9 | 26.8 | 1.2 | 4.2 | 43.1 |

Oxidation of the Iso-propylbenzenes

Acetophenone or p-methyl acetophenone is the major product when the substrates are cumene or p-cymene, respectively. The minor products for oxidation of cumene are 2, 3-dimethyl, 2', 3'-diphenyl butane and ethoxy-methyl benzene. The minor products for oxidation of p-cymene are 4-isopropyl benzyl alcohol, 4-iso-propyl benzaldehyde, and 4-iso-propenyl-toluene.

The oxidation of toluene appears to follow an obvious path as inferred from the kinetics of the product yields (Table IV). The intermediate products are benzyl alcohol, benzaldehyde, benzoic acid; whereas, benzyl benzoate is the final product by esterification of benzyl alcohol and benzoic acid. In a separate test at the same reaction conditions, but without the Pd catalyst, benzyl alcohol and benzoic acid were esterified in toluene to produce benzyl benzoate. The following reaction scheme explains these results:

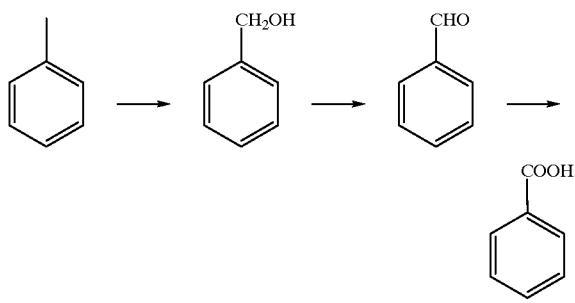

acid-4-methyl benzoic acid ester. Minor products include the coupled products and terephthalaldehyde.

Finally, the oxidation of mesitylene leads to 3, 5-dimethybenzyl alcohol and 3, 5-dimethyl benzaldehyde as the major products. 2, 4, 6-trimethylphenol is a minor product.

The data for the oxidation of the four methylbenzenes substrates suggests that the major reaction products are the result of a sequential oxidation of the benzyl carbon in preference to oxidation of phenyl carbons.

The oxidation of an alkyl substituent having a tertiary carbon leads to the formation of the acetophenone when the substrates were cumene and p-cymene. A carbon is lost from the iso-propyl group during the oxidation.

The present results suggest that the Pd(phen)(OAc)$_2$ catalyst can oxidize the benzyl carbons in preference to the phenyl carbons on substrates that have alkyl groups that can be oxidized further. The date in Table V shows that results of oxidizing toluene over Pd(acac)(OAc) and oxidizing toluene and methyl benzoate over Pd(phen)(OAc)$_2$. The oxidation of toluene over Pd$^{2+}$ with the phen ligand shows products that suggest that the benzyl carbons are oxidized in preference of ring coupling whereas, the oxidation of the same substrate over Pd$^{2+}$ with the acac ligands shows only the products of ring coupling reaction.

TABLE V

Comparison of Oxidations of Aryls over $Pd^{2+}$ Catalysts

| | Substrate | | |
|---|---|---|---|
| Catalyst | toluene Pd(phen)(OAc)$_2$ | toluene Pd(acac)(OAc)$_2$ | methyl benzoate Pd(phen)(OAc)$_2$ |
| Mmol substrate | 327 | 402 | 257 |
| Mmol Pd(II) | 0.5 | 0.5 | 0.5 |
| Mmol ligand | 0.5 | 0.5 | 0.5 |
| Reaction time, min | 240 | 180 | 180 |
| TOF, hr$^{-1}$ | 8 | 13.3 | 6.4 |
| Temperature | 150 | 150 | 150 |
| Yields | | | |
| Benzyl alcohol | 0.15% | 0% | 0% |
| Benzaldehyde | 0.85% | 0% | 0% |
| Benzoic acid | 1.11% | 0% | 0% |
| Benzyl benzoate | 2.77% | 0% | 0% |
| Dimer | 0.06% | 5.0% | 3.7% |

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for the side oxidation of the alkyl groups of compounds of the formula:

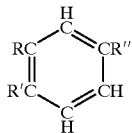

whether R is selected from the group consisting of H, $CH_3$, $C_2H_5$, and i-$C_3H_7$, R' is selected from the group consisting of H and $CH_3$, and R" is selected from the group consisting of H and $CH_3$, wherein no more than two of the Group R, R' and R" is H, said method being conducted in the presence of gaseous oxygen in the presence of the group consisting of palladium phenanthroline acetate catalyst and palladium acetate catalyst with a modified phenanthroline ligand of the formula:

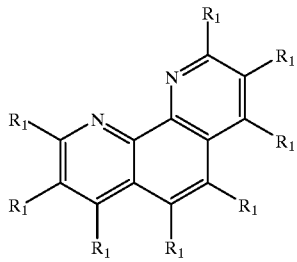

wherein $R_1$ is selected from the group consisting of alkyl groups of from 1 to 3 carbon atoms, OH, and $NO_2$ groups, and halogen and hydrogen atoms with at least six of the $R_1$ groups being hydrogen atoms in the ligand.

2. The method of claim 1, wherein R and R' are H and R" is $CH_3$.

3. The method of claim 1, wherein R and R' are H and R" is $C_2H_5$.

4. The method of claim 1, wherein R' and R' are H and R" is i-$C_3H_7$.

5. The method of claim 1, wherein R1 is hydrogen.

6. The method of claim 1, wherein one of the R1 groups per ligand is methyl and the remainder are hydrogen atoms.

7. The method of claim 1, wherein two of the R1 groups are methyl, and the remaining R1 group per ligands are hydrogen atoms.

* * * * *